(12) United States Patent
Boyle et al.

(10) Patent No.: US 9,107,605 B2
(45) Date of Patent: Aug. 18, 2015

(54) DEVICE FOR IN VIVO DELIVERY OF BIOACTIVE AGENTS AND METHOD OF MANUFACTURE THEREOF

(75) Inventors: Christopher T. Boyle, San Antonio, TX (US); Steven R. Bailey, San Antonio, TX (US); Denes Marton, San Antonio, TX (US); Christopher E. Banas, San Antonio, TX (US)

(73) Assignee: Advanced Bio Prosthetic Surfaces, Ltd., a wholly owned subsidiary of Palmaz Scientific, Inc., Dallas, TX (US)

( * ) Notice: Subject to any disclaimer, the term of this patent is extended or adjusted under 35 U.S.C. 154(b) by 2561 days.

(21) Appl. No.: 10/936,884

(22) Filed: Sep. 9, 2004
(Under 37 CFR 1.47)

(65) Prior Publication Data

US 2005/0186241 A1    Aug. 25, 2005

Related U.S. Application Data

(63) Continuation-in-part of application No. 09/783,633, filed on Feb. 14, 2001, now Pat. No. 8,372,139, and a continuation-in-part of application No. 09/716,146, filed on Nov. 17, 2000, now Pat. No. 8,252,044, and a (Continued)

(51) Int. Cl.
*A61F 2/82* (2013.01)
*A61B 5/07* (2006.01)
(Continued)

(52) U.S. Cl.
CPC .............. *A61B 5/076* (2013.01); *A61B 5/6862* (2013.01); *A61B 5/6876* (2013.01); *A61F 2/82* (2013.01);
(Continued)

(58) Field of Classification Search
CPC ................................................ A61F 2250/0068
USPC .............................. 623/1.39, 1.42–1.45, 1.12
See application file for complete search history.

(56) References Cited

U.S. PATENT DOCUMENTS

| 3,797,485 A | 3/1974 | Urquhart ................ 128/213 |
| 4,203,442 A | 5/1980 | Michaels ................ 128/260 |

(Continued)

FOREIGN PATENT DOCUMENTS

| EP | 0 85218 | 4/1998 | ............. A61F 2/06 |
| EP | 0 850 604 | 7/1998 | ............. A61F 2/06 |

(Continued)

OTHER PUBLICATIONS

Low et al., "Microactuators toward microvalves for responsive controlled drug delivery", Sensors and Actuators, B67 (2000), pp. 149-160.*

(Continued)

*Primary Examiner* — Thomas J Sweet
*Assistant Examiner* — Cheryl Miller
(74) *Attorney, Agent, or Firm* — David G. Rosenbaum; J. Peter Paredes; Rosenbaum IP, P.C.

(57) ABSTRACT

The present invention consists of an implantable structural element for in vivo controlled delivery of bioactive active agents to a situs in a body. The implantable structural element may be configured as an implantable prosthesis, such as an endoluminal stent, cardiac valve, osteal implant or the like, which serves a dual function of being prosthetic and a carrier for a bioactive agent. Control over elution of the bioactive agents occurs through a plurality of cantilever-like cover members which prevent drug elution until an endogenous or exogenous stimulus causes the cover members to open and permit drug elution.

17 Claims, 6 Drawing Sheets

Related U.S. Application Data continuation-in-part of application No. 10/258,087, filed on Aug. 19, 2003, which is a continuation-in-part of application No. 09/716,146, filed as application No. PCT/US01/44642 on Nov. 19, 2001, now Pat. No. 8,252,044.

(51) Int. Cl.

| | |
|---|---|
| *A61F 2/86* | (2013.01) |
| *A61F 2/91* | (2013.01) |
| *A61F 2/915* | (2013.01) |
| *A61L 27/04* | (2006.01) |
| *A61L 27/54* | (2006.01) |
| *A61L 31/02* | (2006.01) |
| *A61L 31/16* | (2006.01) |
| *A61B 5/01* | (2006.01) |
| *A61B 5/0205* | (2006.01) |
| *A61B 5/021* | (2006.01) |
| *A61B 5/0215* | (2006.01) |
| *A61B 5/026* | (2006.01) |
| *A61B 5/00* | (2006.01) |
| *A61F 2/07* | (2013.01) |

(52) U.S. Cl.
CPC ... *A61F 2/86* (2013.01); *A61F 2/91* (2013.01); *A61F 2/915* (2013.01); *A61L 27/04* (2013.01); *A61L 27/54* (2013.01); *A61L 31/022* (2013.01); *A61L 31/16* (2013.01); *A61B 5/01* (2013.01); *A61B 5/021* (2013.01); *A61B 5/026* (2013.01); *A61B 5/0215* (2013.01); *A61B 5/02055* (2013.01); *A61B 5/4839* (2013.01); *A61F 2/07* (2013.01); *A61F 2002/91533* (2013.01); *A61F 2002/91541* (2013.01); *A61F 2002/91558* (2013.01); *A61F 2210/0076* (2013.01); *A61F 2250/0001* (2013.01); *A61F 2250/0067* (2013.01); *A61F 2250/0068* (2013.01); *A61L 2300/602* (2013.01)

(56) References Cited

U.S. PATENT DOCUMENTS

| | | | | |
|---|---|---|---|---|
| 4,309,776 | A | | 1/1982 | Berguer .................. 3/1 |
| 4,479,796 | A | | 10/1984 | Kallok .................. 604/93 |
| 4,995,863 | A | * | 2/1991 | Nichols et al. .................. 604/247 |
| 5,002,661 | A | | 3/1991 | Chick et al. .................. 210/192 |
| 5,061,914 | A | * | 10/1991 | Busch et al. .................. 337/140 |
| 5,062,829 | A | | 11/1991 | Pryor et al. .................. 604/57 |
| 5,180,366 | A | | 1/1993 | Woods .................. 604/96 |
| 5,201,778 | A | | 4/1993 | Brotzu et al. .................. 623/66 |
| 5,224,938 | A | * | 7/1993 | Fenton, Jr. .................. 604/247 |
| 5,234,456 | A | | 8/1993 | Silvestrini .................. 606/194 |
| 5,282,823 | A | | 2/1994 | Schwartz et al. .................. 606/198 |
| 5,304,121 | A | | 4/1994 | Sahatjian .................. 604/53 |
| 5,342,348 | A | | 8/1994 | Kaplan .................. 604/891.1 |
| 5,370,681 | A | | 12/1994 | Herweck et al. .................. 623/1 |
| 5,383,927 | A | | 1/1995 | DeGoicoechea .................. 623/1 |
| 5,383,928 | A | | 1/1995 | Scott et al. .................. 623/1 |
| 5,411,550 | A | | 5/1995 | Herweck et al. .................. 623/1 |
| 5,421,826 | A | | 6/1995 | Crocker et al. .................. 604/53 |
| 5,429,634 | A | | 7/1995 | Narciso, Jr. .................. 604/890.1 |
| 5,441,515 | A | | 8/1995 | Khosravi et al. .................. 606/194 |
| 5,443,458 | A | | 8/1995 | Eury .................. 604/891.1 |
| 5,443,496 | A | | 8/1995 | Schwartz et al. .................. 623/1 |
| 5,449,382 | A | | 9/1995 | Dayton .................. 623/1 |
| 5,500,013 | A | | 3/1996 | Buscemi et al. .................. 623/1 |
| 5,707,385 | A | | 1/1998 | Williams .................. 606/192 |
| 5,843,172 | A | | 12/1998 | Yan et al. .................. 623/1 |
| 5,972,027 | A | | 10/1999 | Johnson .................. 623/1 |
| 6,071,305 | A | * | 6/2000 | Brown et al. .................. 623/1.43 |
| 6,099,561 | A | | 8/2000 | Alt .................. 623/1.44 |
| 6,099,562 | A | | 8/2000 | Ding et al. .................. 623/1.46 |
| 6,143,370 | A | | 11/2000 | Panagiotou .................. 427/422 |
| 6,187,370 | B1 | | 2/2001 | Dinh et al. .................. 427/2.24 |
| 6,203,536 | B1 | | 3/2001 | Berg et al. .................. 604/500 |
| 6,231,516 | B1 | | 5/2001 | Keilman et al. .................. 600/485 |
| 6,231,600 | B1 | | 5/2001 | Zhong .................. 623/1.42 |
| 6,240,616 | B1 | | 6/2001 | Yan .................. 29/527.2 |
| 6,258,121 | B1 | | 7/2001 | Yang et al. .................. 623/1.1 |
| 6,273,908 | B1 | | 8/2001 | Ndondo-Lay .................. 623/1 |
| 6,284,305 | B1 | | 9/2001 | Ding et al. .................. 427/1 |
| 6,287,430 | B1 | | 9/2001 | Matsumoto et al. .................. 204/298.11 |
| 6,287,628 | B1 | | 9/2001 | Hossainy et al. .................. 427/2.3 |
| 6,299,604 | B1 | * | 10/2001 | Ragheb et al. .................. 604/265 |
| 6,358,556 | B1 | | 3/2002 | Ding et al. .................. 427/2.24 |
| 6,387,121 | B1 | | 5/2002 | Alt .................. 623/1.15 |
| 6,399,144 | B2 | | 6/2002 | Dinh et al. .................. 427/2.24 |
| 6,471,721 | B1 | | 10/2002 | Dang .................. 623/1.34 |
| 6,537,310 | B1 | * | 3/2003 | Palmaz et al. .................. 623/1.13 |
| 6,551,838 | B2 | * | 4/2003 | Santini et al. .................. 436/174 |
| 6,902,544 | B2 | * | 6/2005 | Ludin et al. .................. 604/93.01 |
| 7,163,555 | B2 | * | 1/2007 | Dinh .................. 623/1.42 |
| 7,172,622 | B2 | * | 2/2007 | Weber et al. .................. 623/1.12 |
| 7,223,282 | B1 | * | 5/2007 | Hossainy .................. 623/1.15 |
| 7,238,199 | B2 | * | 7/2007 | Feldman et al. .................. 623/1.15 |
| 7,647,090 | B1 | * | 1/2010 | Frisch et al. .................. 600/473 |
| 8,211,092 | B2 | * | 7/2012 | Uhland et al. .................. 604/890.1 |
| 2001/0000802 | A1 | | 5/2001 | Soykan et al. .................. 623/1.13 |
| 2001/0020151 | A1 | | 9/2001 | Reed et al. .................. 604/103.02 |
| 2001/0021415 | A1 | | 9/2001 | Kido et al. .................. 427/255.23 |
| 2002/0007209 | A1 | * | 1/2002 | Scheerder et al. .................. 623/1.15 |
| 2002/0087120 | A1 | * | 7/2002 | Rogers et al. .................. 604/151 |
| 2002/0091440 | A1 | | 7/2002 | Calcote .................. 623/1.42 |
| 2003/0083646 | A1 | * | 5/2003 | Sirhan et al. .................. 604/891.1 |
| 2003/0181853 | A1 | * | 9/2003 | Seward .................. 604/93.01 |
| 2004/0030379 | A1 | | 2/2004 | Hamm et al. .................. 623/1.15 |
| 2004/0082908 | A1 | * | 4/2004 | Whitehurst et al. .................. 604/67 |
| 2004/0143322 | A1 | | 7/2004 | Litvack et al. .................. 623/1.42 |
| 2004/0176742 | A1 | * | 9/2004 | Morris et al. .................. 604/537 |
| 2005/0027350 | A1 | * | 2/2005 | Momma et al. .................. 623/1.42 |
| 2005/0085769 | A1 | * | 4/2005 | MacMahon et al. .................. 604/96.01 |
| 2005/0113798 | A1 | * | 5/2005 | Slater et al. .................. 604/508 |
| 2005/0177223 | A1 | * | 8/2005 | Palmaz .................. 623/1.15 |
| 2005/0203613 | A1 | * | 9/2005 | Arney et al. .................. 623/1.42 |
| 2006/0217798 | A1 | * | 9/2006 | Santini et al. .................. 623/1.42 |

FOREIGN PATENT DOCUMENTS

| | | | |
|---|---|---|---|
| EP | 0 875 218 | 11/1998 | .............. A61F 2/06 |
| EP | 1 132 058 | 3/2000 | .............. A61F 2/06 |
| WO | 97/46268 | 12/1997 | .............. A61F 29/00 |
| WO | 98/13537 | 4/1998 | .............. C25D 1/00 |
| WO | 00/18327 | 4/2000 | .............. A61F 2/06 |
| WO | 00/74584 | 12/2000 | .............. A61B 19/00 |
| WO | 01/12158 | 2/2001 | .............. A61K 9/02 |
| WO | 01/17577 | 3/2001 | .............. A61L 31/14 |
| WO | 01/66036 | 9/2001 | .............. A61F 2/06 |

OTHER PUBLICATIONS

Surbled et al., "Array of Shape Memory Alloy One-Shot Micro-Valves for Drug Delivery", MME99, Gif sur Yvette, France, Sep. 27-28, 1999, pp. 132-135.*

"Local Delivery of Glycoproten lib/IIIa Receptor Inhibitors Using Drug Eluting Stents" by Gershlick, Department of Cardiology, Sep.-Dec. 1998, PMID: 10406691, one page.

"Mechanisms of Drug Loading and Release Kinetics" by Whelan, et al., *Semin Interv Cardiol*, Department of Cardiology Thoraxcenter, Erasmus University Rotterdam, The Netherlands, vol. 3(3-4), Sep.-Dec. 1998, PMID: 10406681, one page.

(56) References Cited

OTHER PUBLICATIONS

"Basic Investigations, Local Drug Delivery of Argatroban From a Polymeric-Metallic Composite Stent Reduces Platelet Depositions in a Swine Coronary Model", by Kruse, et al., *Catheterization and Cardiovascular Interventions*, vol. 46, pp. 503-507 (1999).

"Bioresorbable Microporous Stents Deliver Recombinant Adenovirus Gene Transfer Vectors to the Arterial Wall" by Ye, et al., *Annals of Biomedical Engineering*, vol. 26, pp. 398-408 (1998).

"Biocompatability Aspects of New Stent Technology" by O.F. Bertrand, et al., *JACC*, vol. 32, No. 3, pp. 562-567 (Sep. 1998).

"Local Drug Delivery of Argatroban from a Polymeric-Metallic Composite Stent Reduces Platelet Deposition in a Swine Coronary Model" by Kruse, et al., *Catheter Cardiovascular Intervention*, vol. 46 (4), pp. 503-507 (Apr. 1999).

* cited by examiner

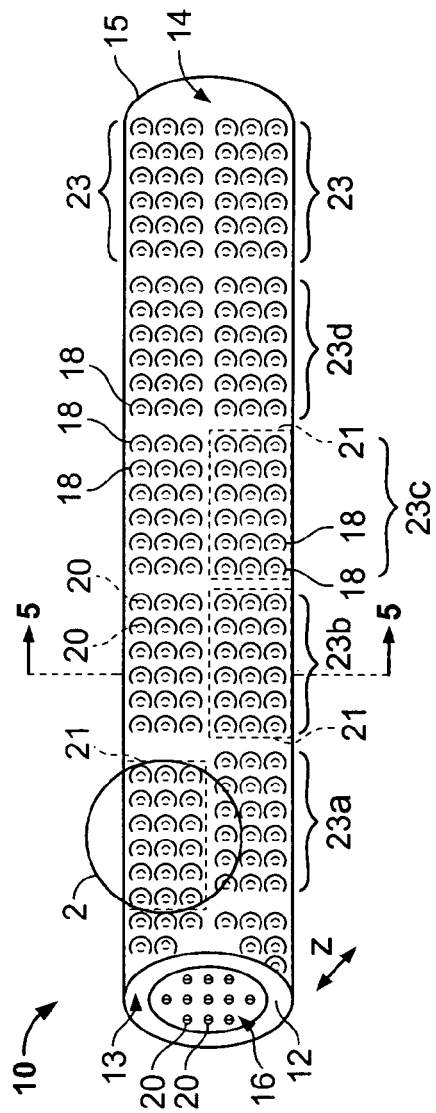
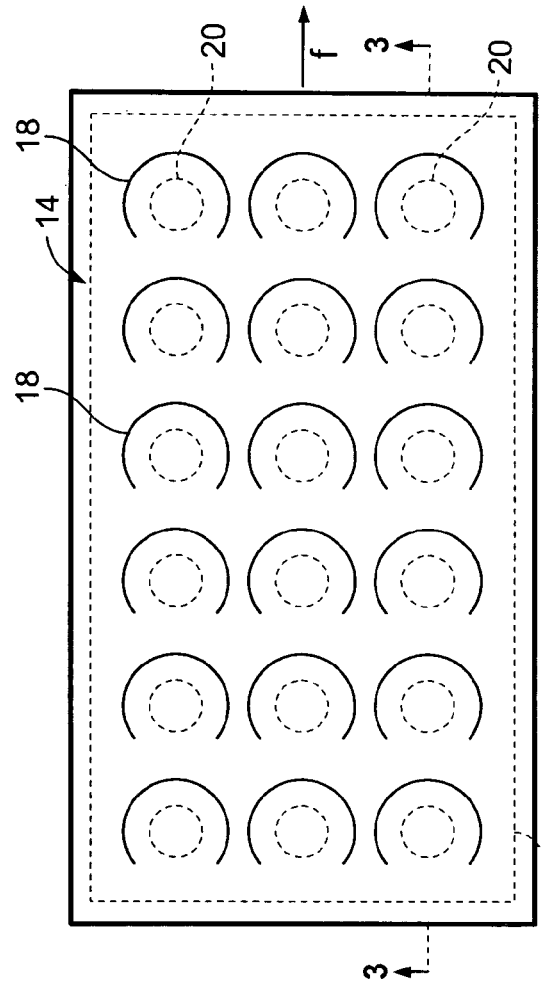
FIG. 1
FIG. 2

DEVICE FOR IN VIVO DELIVERY OF BIOACTIVE AGENTS AND METHOD OF MANUFACTURE THEREOF

CROSS REFERENCE TO RELATED INVENTIONS

This is a continuation-in-part of commonly assigned U.S. patent application Ser. No. 09/783,663 filed Feb. 14, 2001, now U.S. Pat. No. 8,372,139, Ser. No. 09/716,146 filed Nov. 17, 2000, now U.S. Pat. No. 8,252,044, and Ser. No. 10/258,087 filed Oct. 17, 2002, which is a national stage entry of PCT/US01/44642 filed Nov. 19, 2001 and also a continuation-in-part of Ser. No. 09/716,146 filed Nov. 17, 2000, now U.S. Pat. No. 8,252,044.

BACKGROUND OF THE INVENTION

The present invention relates generally to an implantable device for supporting a lumenal passageway and, also, delivering, in vivo, bioactive compounds. More particularly, the present invention relates to an implantable device equipped with cantilever controls for automated delivery of bioactive compounds in response to a predetermined physiological event.

Occlusive diseases, disorders or trauma cause patent body lumens to narrow and restrict the flow or passage of fluid or materials through the body lumen. One example of occlusive disease is arteriosclerosis in which portions of blood vessels become occluded by the gradual build-up of arteriosclerotic plaque, this process is also known as stenosis. When vascular stenosis results in the functional occlusion of a blood vessel the vessel must be returned to its patent condition. Conventional therapies for treatment of occluded body lumens include dilatation of the body lumen using bioactive agents, such as tissue plasminogen activator (TPA) or vascular endothelial growth factor (VEGF) and fibroblast growth factor (FGF) gene transfers which have improved blood flow and collateral development in ischemic limb and myocardium (S. Yla-Herttuala, *Cardiovascular gene therapy*, Lancet, Jan. 15, 2000), surgical intervention to remove the blockage, replacement of the blocked segment with a new segment of endogenous or exogenous graft tissue, or the use of a catheter-mounted device such as a balloon catheter to dilate the body lumen or an artherectomy catheter to remove occlusive material. The dilation of a blood vessel with a balloon catheter is called percutaneous transluminal angioplasty. During angioplasty, a balloon catheter in a deflated state is inserted within an occluded segment of a blood vessel and is inflated and deflated a number of times to expand the vessel. Due to the inflation of the balloon catheter, the plaque formed on the vessel walls cracks and the vessel expands to allow increased blood flow through the vessel.

In approximately sixty percent of angioplasty cases, the blood vessel remains patent. However, the restenosis rate of approximately forty percent is unacceptably high. Endoluminal stents of a wide variety of materials, properties and configurations have been used post-angioplasty in order to prevent restenosis and loss of patency in the vessel.

While the use of endoluminal stents has successfully decreased the rate of restenosis in angioplasty patients, it has been found that a significant restenosis rate continues to exist even with the use of endoluminal stents. It is generally believed that the post-stenting restenosis rate is due, in major part, to a failure of the endothelial layer to regrow over the stent and the incidence of smooth muscle cell-related neointimal growth on the luminal surfaces of the stent. Injury to the endothelium, the natural nonthrombogenic lining of the arterial lumen, is a significant factor contributing to restenosis at the situs of a stent. Endothelial loss exposes thrombogenic arterial wall proteins, which, along with the generally thrombogenic nature of many prosthetic materials, such as stainless steel, titanium, tantalum, Nitinol, etc. customarily used in manufacturing stents, initiates platelet deposition and activation of the coagulation cascade, which results in thrombus formation, ranging from partial covering of the luminal surface of the stent to an occlusive thrombus. Additionally, endothelial loss at the site of the stent has been implicated in the development of neointimal hyperplasia at the stent situs. Accordingly, rapid re-endothelialization of the arterial wall with concomitant endothelialization of the body fluid or blood contacting surfaces of the implanted device is considered critical for maintaining vasculature patency and preventing low-flow thrombosis. To prevent restenosis and thrombosis in the area where angioplasty has been performed, anti-thrombosis agents and other biologically active agents can be employed.

It has been found desirable to deliver bioactive agents to the area where a stent is placed concurrently with stent implantation. Many stents have been designed to delivery bioactive agents to the anatomical region of stent implantation. Some of these stents are biodegradable stents which are impregnated with bioactive agents. Examples of biodegradable impregnated stents are those found in U.S. Pat. Nos. 5,500,013, 5,429,634, and 5,443,458. Other known bioactive agent delivery stents include a stent disclosed in U.S. Pat. No. 5,342,348 in which a bioactive agent is impregnated into filaments which are woven into or laminated onto a stent. U.S. Pat. No. 5,234,456 discloses a hydrophilic stent that may include a bioactive agent adsorbed which can include a biologically active agent disposed within the hydrophilic material of the stent. Other bioactive agent delivery stents disclosed in U.S. Pat. Nos. 5,201,778, 5,282,823, 5,383,927; 5,383,928, 5,423,885, 5,441,515, 5,443,496, 5,449,382, 4,464,450, and European Patent Application No. 0 528 039. Other devices for endoluminal delivery of bioactive agents are disclosed in U.S. Pat. Nos. 3,797,485, 4,203,442, 4,309,776, 4,479,796, 5,002,661, 5,062,829, 5,180,366, 5,295,962, 5,304,121, 5,421,826, and International Application No. WO 94/18906. A directional release bioactive agent stent is disclosed in U.S. Pat. No. 6,071,305 in which a stent is formed of a helical member that has a groove in the abluminal surface of the helical member. A bioactive agent is loaded into the groove prior to endoluminal delivery and the bioactive agent is therefore in direct apposition to the tissue that the bioactive agent treats. Finally, International Application No. WO 00/18327 discloses a drug delivery stent in which a tubular conduit is wound into a helical stent. The tubular conduit has either a single continuous lumen or dual continuous lumens that extend the entire length of the conduit. The tubular conduit has regions or segments thereof that has pores to permit drug "seepage" from the conduit. One end of the tubular conduit is in fluid flow communication with a fluid delivery catheter, which introduces a fluid, such as drug into the continuous lumen and through the pores.

Where biodegradable or non-biodegradable polymer-based or polymer-coated stents have been used, the polymers cause an immune inflammatory response once the drug is eluted out of the polymer. Where a polymer is employed as the bioactive agent carrier, it is, therefore, desirable to isolate the polymer from body tissues in order to limit the immune inflammatory response after the bioactive agent has eluted as can be accomplished with the present invention.

There still remains a need for an implantable medical device that can support a physiological lumen and automatically deliver a bioactive agent upon need, the need defined by a significant physiological event. More specifically, there is a need for an implantable medical device that allows for controlled delivery of a bioactive agent. Also, there is a further need for an implantable medical device that can detect a significant physiological event and can be manually activated to deliver a bioactive agent in a noninvasive manner.

SUMMARY OF THE INVENTION

The present invention is directed, generally, to an implantable medical device which is deliverable within an anatomical passageway and is capable of restoring and maintaining patency of the anatomical passageway and delivering a bioactive agent within the anatomical passageway. While not limiting the present invention, a common use for the present invention is as a coronary or other vascular stent device which is percutaneously delivered to a situs within the body's vascular system using catheter-based approaches and, once implanted at the desired situs, is capable of releasing a bioactive agent to facilitate and promote a healing response within damaged or injured regions of the vasculature.

More particularly, the present invention is adapted to delivery the bioactive agent in response to either an endogenous condition or conditions or an exogenous condition or conditions. For example, endogenous conditions which may initiate drug delivery include, without limitation, certain physiological conditions such as growth of non-endothelial cells on the device, inflammatory responses, vascular wall pressure or the presence of T-cells or natural killer cells. Non-limiting examples of exogenous conditions which may initiation drug delivery include applied RF fields, magnetic fields, electromagnetic fields, ultrasound, x-ray, positron emissions, laser or photon emissions.

In accordance with the present invention there is provided a structural body, preferably a generally tubular member, having at least one internal chamber or cavity within the structural body and a plurality of openings passing through the structural body and communicating between an external wall surface of the structural body and the at least one internal chamber. A plurality of cantilever members are provided on or are formed in a wall surface of the structural body and are positioned such that each cantilever member is superimposed over and covering at least one of the plurality of openings.

The plurality of cantilever members consist generally of flap-like members which are preferably fabricated of shape memory or superelastic material, and have binary functionality, i.e., are either in an open or a close position. Each of the plurality of cantilever members may be MEMS (micro-electromechanical systems) devices responsive to defined stimulus, such as temperature or pressure, and may be derivitized by attachment of reactive moieties having binding affinity for specific biochemical markers. As noted, each of the cantilever members have binary functionality. In a first or closed position the cantilever members covers and occludes at least one associated opening that passes through the wall of the structural body an communicates with the internal chamber or cavity retaining the bioactive agent within the structural body. In the second or open position, the cantilever deflects and uncovers the opening or openings with which it is associated, thereby permitting the bioactive agent to elute from the opening or openings. The second or open position of the cantilever occurs as a result of either the presence or absence of a pre-determined stimulus. For example, the second position may be responsive to flow pressure, such as blood flow, such that cessation or diminution of blood flow resulting from tissue growth or occlusion, activates the second position. Alternatively, the second position may be responsive to temperature such that thermal induction, such as that induced by ultrasound resonance, may activate the second position.

After the cantilever members assume their open position, elution of the bioactive agent from the internal chamber or cavity and out of the uncovered plurality of openings may occur through a number of mechanisms, including, without limitation, free flow, pumped or pulsed flow, osmotic-mediated diffusion, capillary diffusion, displacement flow or the like.

As used herein the term "bioactive agent" is intended to include one or more pharmacologically active compounds which may be in combination with pharmaceutically acceptable carriers and, optionally, additional ingredients such as antioxidants, stabilizing agents, permeation enhancers, and the like. The terms "pharmacologically active agents" and "bioactive agent" as used herein are used synonymously with "drug(s)". Examples of bioactive agents which may be used in the present invention include but are not limited to antiviral drugs, antibiotic drugs, steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator (TPA), urokinase, hirudin, streptokinase, antiproliferative agents such as methotrexate, cisplatin, fluorouracil, ADRIAMYCIN, antioxidants such as ascorbic acid, beta carotene, vitamin E, antimetabolites, thromboxane inhibitors, non-steroidal and steroidal anti-inflammatory drugs, immunosuppresents, beta and calcium channel blockers, genetic materials including DNA and RNA fragments, complete expression genes, antibodies, lymphokines, growth factors, such as vascular endothelial growth factor (VEGF) and fibroblast growth factor (FGF), prostaglandins, leukotrienes, laminin, elastin, collagen, nitric oxide (NO), integrins, paclitaxel, taxol, rapamycin, rapamycin derivatives, such as those disclosed in U.S. Patent Application Publication 2003/0170287 published Sep. 11, 2003, sirolimus, rapamune, tacrolimus, dexamethasone, everolimus, ABT-578 (a rapamycin analogue that inhibits the mTOR cell cycle regulatory protein), and growth factors, such as VEG-F.

A further aspect of the present invention is the provision of a diametrically changeable structural member. The structural member may assume a cylindrical, tubular, planar, spherical, curvilinear or other general shape which is desired and suited for a particular implant application. For example, in accordance with the present invention there is provided an endoluminal stent that is made of a plurality of interconnected members commonly referred to struts or circumferential rings that define a generally tubular shape for the endoluminal stent. At least some of the plurality of interconnected members are fabricated in such a manner as to have least one internal cavity defined within or on the interconnected members or their interconnection members and at least one opening which communicates between the internal cavity and external the stent. Alternate types of implantable devices contemplated by the present invention include, without limitation, covered stents, stent-grafts, grafts, heart valves, venous valves, filters, occlusion devices, catheters, osteal implants, implantable contraceptives, implantable anti-tumor pellets or rods, or other implantable medical devices.

In one aspect of the present invention, there exists a stent for delivery of bioactive agents, which consists, in general, of a plurality of structural elements, at least some of which have internal cavities that retain the bioactive agents, and openings that pass between the internal cavities and the surface of the structural elements to communicate the bioactive agent from the internal cavity to external the stent. Other than described herein, the present invention does not depend upon the particular geometry, material, material properties or configuration of the stent.

Another aspect of the present invention relates to sensors that may be incorporated onto the implantable medical device, or more specifically, onto the cantilever, to monitor or detect either an endogenous or exogenous stimulus. The endogenous stimulus will, typically, be a physiological event, such as smooth muscle cell proliferation, endothelialization, plaque formation, biochemical changes, cell or cell surface protein binding, or the like. The sensors are preferably fabricated via thin film vacuum deposition, either as a monolithic monolayer of material or a multilayered film, wherein at least portions of the film are capable of sensing at least one of changes in fluid flow, fluid flow rate, temperature, pressure, or the presence or absence of chemical or biochemical species in the body by mechanical, electrical, chemical, electrochemical or electromechanical means.

Specifically, the sensors allow the monitoring of clinically significant physiological events based upon physical, chemical or electrical energy differences present in a body passageway. For example, the sensors of the present invention may be employed to sense significant changes to blood flow volume, blood flow rate, pressure, electrical energy, biochemical interactions, temperature, or to the degree and type of deposits within the lumen of an endoluminal implant, such as a stent or other type of endoluminal conduit. The present invention also provides a means to modulate mechanical and/or physical properties of the endoluminal implant in response to the sensed or monitored parameter. For example, where the monitored blood flow volume through an endoluminal device is determined to be below physiological norms and/or the blood pressure is determined to be above physiological norms, the implantable medical device, such as a stent, may be triggered to release a selected bioactive agent, whether automatically or manually controlled.

In one aspect of the invention, the sensors allow for monitoring the environment around the implantable device to detect stimuli indicative of predetermined events. In a preferred aspect, the sensors are fabricated onto or in association with the plurality of cantilever members. Upon detecting the particular event, a signal can be delivered towards the implantable device that then triggers the cantilever to undergo transformation from the closed to open position. Upon transformation, the selected bioactive agent can is released into the local environment.

In another aspect of the invention, the sensors also detect the predetermined stimulus, but instead of simply monitoring, the sensor signals or transfers energy to the cantilever causing the cantilever to undergo a physical transformation from the closed to open position. Preferably, the cantilever is fabricated to act as the sensor itself so that once the cantilever detects the energy contributing event, the cantilever responds to the energy contributing event and undergoes physical transformation from the closed to open position.

In accordance with another embodiment of the invention, the inventive sensor comprises at least one region of the implantable endoluminal device that is formed of a plurality of cantilever members having different mechanical properties, such as different modulus of elasticity, plasticity or stress-strain behaviors. In accordance with the best mode presently contemplated for the invention, the cantilever members are preferably fabricated of a superelastic material. As with the shape-memory cantilever members, the superelastic cantilever members may be positioned on either a fluid contacting or tissue contacting surface of the implantable device, such as the luminal surface of a stent which contacts blood, or on the abluminal surface of a stent which contacts neointimal tissue of the blood vessel. Alternatively, the sensors may be positioned on both the fluid contacting and the tissue-contacting surface of the implantable device. Unlike the shape-memory cantilever sensors, the superelastic cantilever sensors are responsive to changes in force, such as shear forces, applied to the sensors.

With both the shape-memory cantilever members sensor and the superelastic cantilever members sensor, each of the plurality of cantilever members have first and second positions that are indicative of either a closed or open position, respectively. The first or "closed" position of each cantilever members is coplanar or flush with the surface of the endoluminal device into which the sensor is positioned. In the second or "open" position, each activated cantilever members projects outwardly from the surface of the endoluminal device into which the sensor is positioned. Because different cantilever members or groups of cantilever members are fabricated to have either different transition temperatures or different stress-strain properties, individual cantilever members or groups of cantilever members which are in the second or "open" position, are indicative of a given thermal or stress-strain condition existing within the body into which the endoluminal device is implanted and allows for the release of bioactive agent housed in the internal cavities.

In one particular form of the invention, the inventive endoluminal device comprises a temperature sensor having a plurality of cantilever members positioned on at least one of the proximal, distal or intermediate regions of the endoluminal device and positioned on at least one of the luminal or abluminal wall surfaces of the endoluminal device. To facilitate ease of detection, a plurality of groups of cantilever members are provided, each group is formed of a plurality of individual cantilever members, with each individual cantilever members in the group having identical transition temperatures. The plurality of groups of cantilever members are arrayed along the longitudinal axis of the endoluminal device in such a manner as to create a continuum of groups of cantilever members having different transition temperatures. Changes in temperature at the site of the endoluminal device are indicated by the position of the cantilever members or groups of cantilever members as determined by radiography, ultrasonography, magnetic resonance imaging or other means that provides a detectable image of the position of the cantilever members and groups of cantilever members.

In another particular form the invention, the sensor comprises a plurality of cantilever members positioned on at least one of the proximal, distal or intermediate regions of the endoluminal device and positioned on at least one of the luminal or abluminal wall surfaces of the endoluminal device. To facilitate ease of detection, a plurality of groups of cantilever members are provided, each group is formed of a plurality of individual cantilever members, with each individual cantilever members in the group having identical transition temperatures. The plurality of groups of cantilever members are arrayed along the longitudinal axis of the endoluminal device in such a manner as to create a continuum of groups of cantilever members having different stress-strain transition pressures. Changes in applied stress or strain, such as blood pressure or blood flow shear stress, at the site of the endoluminal device are indicated by the stress and strain acting on the cantilever members or groups of cantilever members which provides a corresponding frequency shift in energy reflected, when compared to a baseline stress-strain for unloaded cantilever members. The position and frequency shift of the cantilever members may be determined by radiography, ultrasonography, magnetic resonance imaging or other means which provides a detectable image of the position of the individual cantilever members and groups of cantilever members or is capable of measuring frequency shifts due to differential stress-strain loading onto the cantilever members.

In yet another form of the invention, the inventive sensor is a biosensor that is microfabricated from a material capable of undergoing elastic, plastic, shape-memory or superelastic deformation, and has a plurality of cantilever members formed therein, as described above. Each of the plurality of cantilever members has at least one binding domain selective for at least one indicator of endothelialization selected from the group of endothelial cell surface proteins, antigens, antibodies, cytokines, growth factors, co-factors, or other biological or biochemical marker of endothelial cells or endothelial cell precursors. Binding of the at least one indicator to at least one of the plurality of cantilever members causes a change in strain applied to the cantilever members, thereby causing the relevant cantilever members or groups of cantilever members to undergo superelastic transformation from the first or "closed" position to the second or "open" position. As with the above-described embodiments of the invention, the position of the sensor cantilever members in the second or "open" position relative to the endoluminal device is indicative of the progress of endothelialization and allows for release of bioactive agents housed in the internal cavities.

Similarly, the fact of or the progress of atherosclerotic plaque formation may be sensed and treated with the appropriate bioactive agent by using a plurality of elastic or superelastic cantilever members. In accordance with a first embodiment, the plurality of superelastic cantilever members undergo martensitic transformation as a result of the strain applied to the cantilever members resulting from growth of atherosclerotic plaque onto the cantilever members. In accordance with a second embodiment, the plurality of superelastic cantilever members has at least one binding domain selective for at least one indicator of atherosclerotic plaque or its precursors. Binding of the atherosclerotic plaque or precursors of atherosclerotic plaque to the binding domain on the cantilever members, adds a quantum of strain to the cantilever members sufficient to cause the cantilever members to undergo superelastic transformation from the first or "closed" position to the second or "open" position. As with the above-described embodiments of the invention, the position of the sensor cantilever members in the second or "open" position relative to the endoluminal device is indicative of the progress of arteriosclerosis and results in the release of the appropriate bioactive agent housed in the internal cavities.

Because of their use as a structural scaffold and the requirement that stents be delivered using transcatheter approaches, stents necessarily are delivered in a reduced diametric state and are expanded or allowed to expand in vivo to an enlarged diametric state. Thus, all stents have certain structural regions that are subject to higher stress and strain conditions than other structural regions of the stent. Thus, it may be advantageous to position the internal cavities that retain the bioactive agents in structural regions of the stent that are subjected to relatively lower stress and strain during endoluminal delivery and deployment. Alternatively, where delivery of a bolus of a bioactive agent is desired, internal cavities may be positioned in regions that undergo large deformation during delivery and deployment thereby forcing the bioactive agent out of the internal cavity under the positive pressure exerted by the deformation. Diffusion forces, then, elute remaining bioactive agent present in either the region of large deformation or the regions of lower stress and strain.

BRIEF DESCRIPTION OF THE DRAWINGS

FIG. 1 is a perspective view of an implantable member having a plurality of cantilever members in accordance with the present invention.

FIG. 2 is a fragmentary plan view taken from area 2 of FIG. 1.

DETAILED DESCRIPTION OF THE PREFERRED EMBODIMENTS

Figure 3:
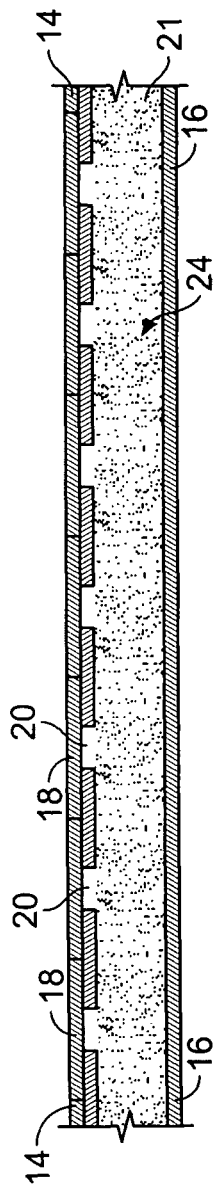
FIG. 3 is a cross-sectional view taken along line 3-3 of FIG. 2 illustrating the a plurality of cantilever members in a first or closed position.

With particular reference to FIGS. 1 and 2, the drug-eluting device 10 of the present invention consists generally of a body element 12, which for purposes of illustration only, is depicted in a generally tubular conformation having a first wall surface 14 and a second wall surface 16, a first end surface 13 and an opposing second end surface 15. A plurality of openings 20 pass through either or both of the first wall surface 14 and the second wall surface 16 and communicate between at least one chamber 21, shown in phantom, which resides entirely within the z-axis thickness of the drug-eluting device 10 and is defined between the first wall surface 14 and the second wall surface 16 with only at least one of the plurality of openings 20 communicating between the internal chamber 21 and either the first 14 or second 16 wall surface of the drug-eluting device 10. A plurality of cover members 18 are provided in or in association with either or both of the first wall surface 14 and the second wall surface 16, and are positioned such that at least one of the plurality of openings 20 are covered by one of the plurality of cover members 18. The plurality of openings 29 and the associated plurality of cover members 18 may, optionally, be arrayed in a pattern of groupings 23a-23e of openings 20 and cover members 18. Each of the plurality of cover members 18 have generally binary functionality in that they have a first or closed position where the associated at least one opening 20 is covered and occluded by the cover member 18, and a second or open position where the associated at least one opening 20 is uncovered by the cover member 18. Transition between the first position and the second position preferably occurs by either shape memory or superelastic phase transitions in the material used to fabricate the plurality of openings 20. The binary transition of the plurality of cover members 18 may be synchronous or asynchronous. That is, that all of the plurality of cover members 18 may transition between the first to the second position under common conditions and, therefore, act synchronously; alternatively, either individual cover members 18 or groups of cover members, but not all cover members 18, may transition under common conditions, while other cover members 18 do not undergo a binary transition, therefore, acting asynchronously.

While the drug-eluting device 10 of the present invention is illustrated and will be described with reference to a generally tubular embodiment, those of ordinary skill in the art will understand and appreciate that alternate geometric conformations are contemplated and feasible, including, without limitation, spherical, ovoid, planar, curvilinear or cylindrical conformations.

In accordance with a preferred embodiment of the present invention, the plurality of cover members 18 comprise cantilever-like members fabricated of shape memory or superelastic metal or pseudometal material. The cantilever-like cover members 18 may be formed as integral components in the first wall surface 14, the second wall surface 16, or both, may be formed as a layer upon the first wall surface 14, the second wall surface 16 or both, or, alternatively, may be discrete members which may be coupled to the first wall surface 14, the second wall surface 16, or both. Further, the cantilever-like cover members may be provided in regular or irregular pattern arrays. The cantilever 15 can cover any or all openings 14 in any desired pattern. Additionally, some of the plurality of openings 20 may have no associated cantilever-like cover member 18, or all of the plurality of openings 20 may have associated cantilever-like cover members 18. The plurality of openings 20 have dimensions sufficient to permit the bioactive agent to elute by diffusion, osmotic pressure or under the influence of a positive pressure applied by cellular in-growth into the at least one interior chamber 21.

Figure 4:
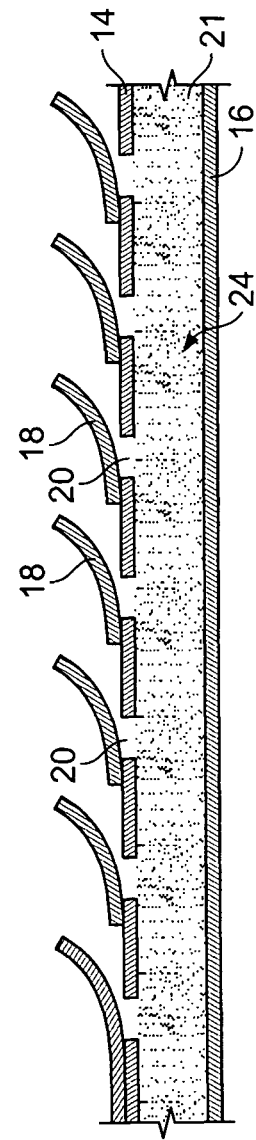
FIG. 4 is the same cross-sectional view as in FIG. 3, illustrating the plurality of cantilever members in a second or open position.

FIGS. 3 and 4 illustrate the binary functioning of the plurality of cantilever-like cover members 18. In the embodiments illustrated in FIGS. 3 and 4, the plurality of cantilever-like cover members 18 are formed integrally in wall surface 14, and each of the plurality of cantilever-like cover members 18 subtend an associated opening 20 which underlies the cover member 18. Those skilled in the art will appreciate that openings 20 and cover members 18 could also be formed in and associated with opposing wall surface 16. The interior chamber 21 is defined entirely within the Z-axis thickness of the device 10 and intermediate the first wall surface 14 and the second wall surface 16. An elutable bioactive agent 24 is retained with the interior chamber 21. FIG. 3 illustrates the plurality of cantilever-like cover members 18 in their first or closed position where each of the plurality of cantilever-like cover members 18 are in co-planar relationship with one another along wall surface 14. FIG. 4 illustrates the plurality of cantilever cover members 18 in their second or open position where each of the plurality of cantilever-like cover members are deformed to uncover each associated opening 20, and permit elution of the bioactive agent 24 from the interior chamber 21 and through the openings 20. As noted above, while FIGS. 3 and 4 depict synchronous function of the plurality of cantilever-like cover members 18, the plurality of cantilever-like cover members 18 may function asynchronously.

Figure 5:
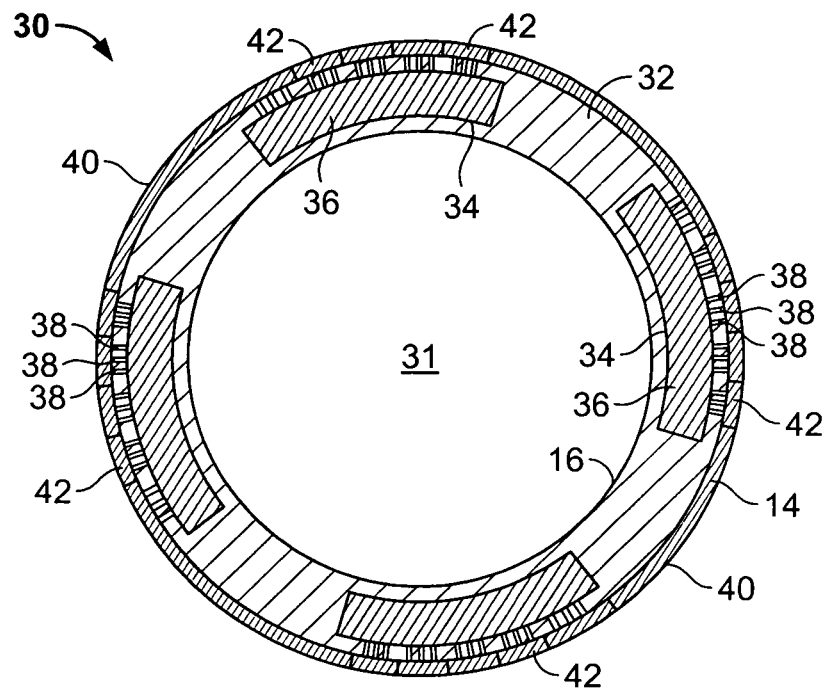
FIG. 5 is a cross-sectional view taken along line 5-5 of FIG. 1.

FIG. 5 is a transverse cross-sectional view taken along line 5-5 of FIG. 1 and illustrates the drug-eluting implantable device 30 in an embodiment consisting of a generally tubular member 32, which may be a cylindrical member, or may be an individual strut of a stent. The tubular member 32 has at least one of a plurality of internal chambers 34 formed entirely between a first wall surface 14 and a second wall surface 16 of the tubular member 32 which act as a reservoir for a bioactive agent 36. A central lumen 31 provides a fluid flow channel for bodily fluids to traverse the device 30. Alternatively, where the tubular member 32 may be an individual strut of a stent, the central lumen 32 may serve as the internal chambers 34 for retaining the bioactive agent 36 to be eluted from the device 30, in which case, the plurality of internal chambers 24 may, optionally, be eliminated. The plurality of openings 38 communicate between the at least one of a plurality of internal chambers 34, the central lumen 31 and external the device 30. The plurality of cantilever-like cover members 42 are formed in an outer circumferential layer 40 which forms the first wall surface 14 of device 30.

Figure 6:
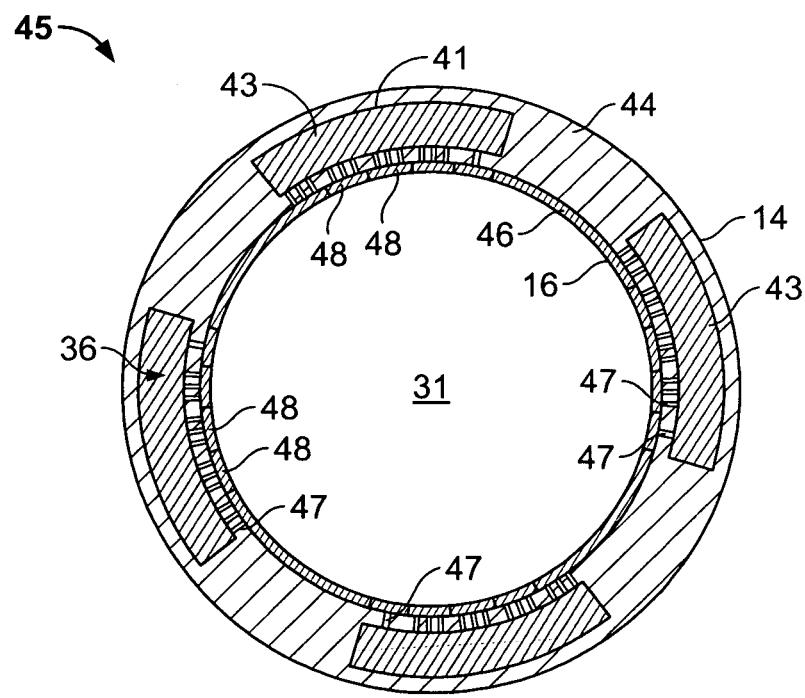
FIG. 6 is a cross-sectional view of an alternate embodiment of the present invention.

FIG. 6 is a transverse cross-section view of an alternate embodiment of the invention depicted in FIG. 5. The alternative embodiment of the drug-eluting device 45 depicted in FIG. 6 is substantially similar to that in FIG. 5, with the exception that the plurality of openings 47 communicate between the plurality of interior chambers 43 and central lumen 31 of the device 45. Additionally, the plurality of cantilever-like members 48 are formed in a lumenal layer of material 46 and cover the plurality of openings 47 to control elution of the bioactive agent 36 from the interior chambers 43. Thus, in FIG. 5, when at least some of the plurality of cantilever-like cover members 42 transition from their first, closed position to their second, open position, the bioactive agent 36 is eluted abluminally from the device 30, while in FIG. 6, the bioactive agent 36 is eluted luminally from the device 45.

The position of each of the plurality of openings 20 may vary dependent upon the particular indication or application for which the drug-eluting implantable device 10 is intended. The plurality of openings 20 may open to either a luminal wall surface 16 of the device 10, or to an abluminal wall surface 14 of the device 10, or both the luminal wall surface 16 and the abluminal wall surface 14 of the device 10. As an alternative to having a uniform distribution of openings 20 about the circumferential and longitudinal axes of the device 10, there may be provided a higher density of openings 20 toward a proximal or distal end of the device 10. Alternatively, a higher density of openings 20 may be provided along an intermediate region of the device 10. It will be understood that where there is provided a higher density of openings 20, a larger dosage of the bioactive agent 36 may be released at any one time due to the higher density of openings 20.

In addition to the foregoing positioning of the plurality of openings 21, the plurality of internal chambers 34, 41, may be either continuous or discontinuous within the z-axis thickness of the device 10 and may be present in different circumferential or longitudinal regions of the device 10. Where discontinuous internal chambers 34, 41 are provided, plural bioactive agents may be loaded into the device 10 for either synchronous or asynchronous elution.

By employing asynchronous functioning plurality of cantilever-like cover members 18, differential drug delivery may be accomplished based upon occurrence of different physiological conditions.

The body element 12 is preferably fabricated of a biocompatible metal such as titanium, vanadium, aluminum, nickel, tantalum, zirconium, chromium, silver, gold, silicon, magnesium, niobium, scandium, platinum, cobalt, palladium, manganese, molybdenum and alloys thereof, such as zirconium-titanium-tantalum alloys, nickel-titanium alloy, chromium-cobalt alloy or stainless steel. The plurality of cantilever-like cover members 18 are preferably fabricated of a shape memory or superelastic material, such as nickel-titanium or chromium cobalt alloy.

Each of the plurality of cantilevers 18 may be fabricated of a material capable of undergoing elastic, plastic, shape memory and/or a superelastic deformation. Materials such as stainless steel, titanium, nickel, tantalum, gold, vanadium, nickel-titanium, or alloys thereof may be employed to fabricate the plurality of cantilever members. Different electrical, thermal or mechanical properties may be imparted to the cantilevers 18 by altering the alloy ratios of the material. It is preferable to vacuum deposit both the body element 12 and cantilevers 18 to permit tight control over the material composition, electrical, mechanical and thermal properties of the material, as well as provide for tight control over the tissue and fluid contacting surfaces and the bulk material of the device. For example with nickel-titanium alloys, the titanium content of the target, in a nickel-titanium binary target, may be changed a known amount to precisely alter the transition temperature of a cantilever members 18.

In accordance with one embodiment of the present invention either or both of the body member 12 and the plurality of cantilevers 18 are fabricated of thin metallic films. As used herein, the term "thin metallic film" or "metal thin film" are used synonymously to refer to biocompatible materials made of metallic or pseudometallic materials. The inventive thin metallic films may be fabricated by conventional wrought metal processing techniques, or may be made by nanofabrication techniques such as physical vapor deposition or chemical vapor deposition. Such thin metallic films as are used with the present invention may be comprised of single or plural layer films fabricated of biocompatible metals or biocompatible pseudometals having thicknesses greater than 0 µm and less than about 125 µm.

Each of the plurality of cantilevers 18 preferably have binary functionality to provide a first "closed" position indicative of an austenite phase of the cantilevers 18 and a second "open" position indicative of a martensite phase of the cantilevers 18. The closed position is configured such that it is in a lowered position that is substantially co-planar with the surface. On the other hand, the open position is configured such that it is in the raised position or projecting outwardly relative to the surface.

It will be understood, therefore, that as the implanted temperature sensor encounters different in vivo temperatures, different sets of cantilever members will be exposed to their transition temperature and change from the "closed" position to the "open" position. Once in the open position, the cantilevers do not impede elution of bioactive agents through the openings from the internal cavities.

The plurality of cantilever-like cover members 18 function as sensors in that they may be fabricated to sense and respond to changes in a physiological state, such as pressure, temperature, cell or protein binding, the presence or absence of a given biochemical marker, or the like. Alternatively, the plurality of cantilever-like cover members 18 may be fabricated to respond only to a specific externally applied stimulus. In this manner, an exogenous stimulus, such as a magnetic field, RF energy, ultrasound, heat or the like may be applied to actuate at least some of the plurality of cantilever-like cover members 18 and permit elution of the bioactive agent.

As illustrated in FIG. 1, ordered arrays, generally denoted as element 23, of cantilever like cover members 18 may form sensor groups, such that, for example, a cantilever-like cover members 18 forming a first array 23*a* may be fabricated to have a martensitic stress/strain transition coefficient $\sigma$, while cantilever-like cover members 18 forming second array 23*b* are fabricated to have a transition coefficient $\sigma+1$, cantilever-like cover members 18 forming a third array 23*c* are fabricated to have a transition coefficient of $\sigma+2$, etc. such that different cover members 18 or groups of cover members 18 change their position based upon a given quantum of stress or strain applied to the cantilever-like cover members 18 in vivo.

Alternatively rather than having merely binary functionality, each of the plurality of cover members 18 may have a response curve which is dependent upon the modulus of the material and the moment of inertia of each cantilever member. This response curve allows for varying degrees of impedance of the openings as the cover members 18 gradually shift from a closed to opening position, thereby, resulting in varying elution profiles through the openings. Each of the cover members 18 may be configured to have a variation in Z-axis thickness along an X-Y axis of the cover members 18. By configuring the cover members 18 with variable Z-axis thicknesses, different cover members 18 or different groupings of cover members 18 will exhibit different stress-strain responses due to the different material modulus and different moment of inertia attendant to the altered geometry of the cover members 18. With this alternate construct of the cover members 18, for a given quantum of stress-strain applied to the cover members 18, the cover members 18 will deflect and shift a returned resonance frequency applied from an external energy source. The degree of deflection will then correlate to the stress and strain forces acting upon the cover members 18. It will be understood, of course, that this alternate construct of the cover members 18 still provides binary "closed" and "open" functionality with the "closed" and "open" positions merely being indicative of the outlying positions of the cover members 18.

It will be understood, therefore, that as the implanted sensor encounters different stress and strain associated with, for example, changes in physiological blood pressure, fluid shear stress, endothelialization, arterioschlerotic plaque development, different sets of cantilever members will be exposed to their transition conditions and change from the "closed" position to the "open" position.

Figure 7:
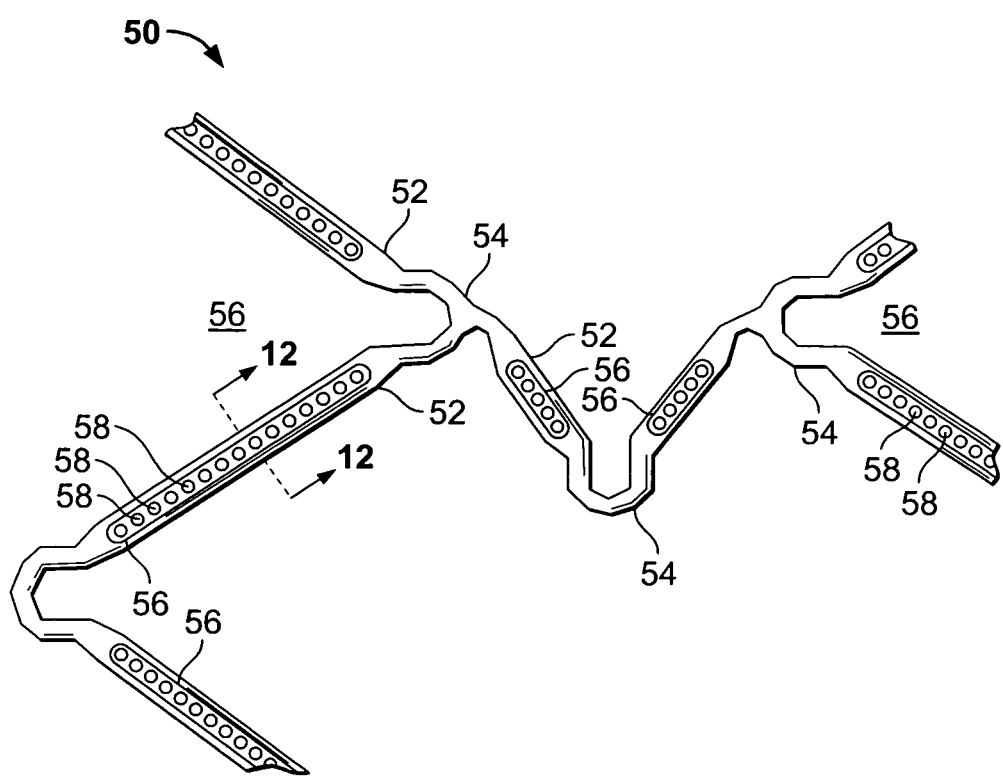
FIG. 7 is a fragmentary plan view of a drug-eluting stent in accordance with a preferred embodiment of the present invention.
Figure 8:
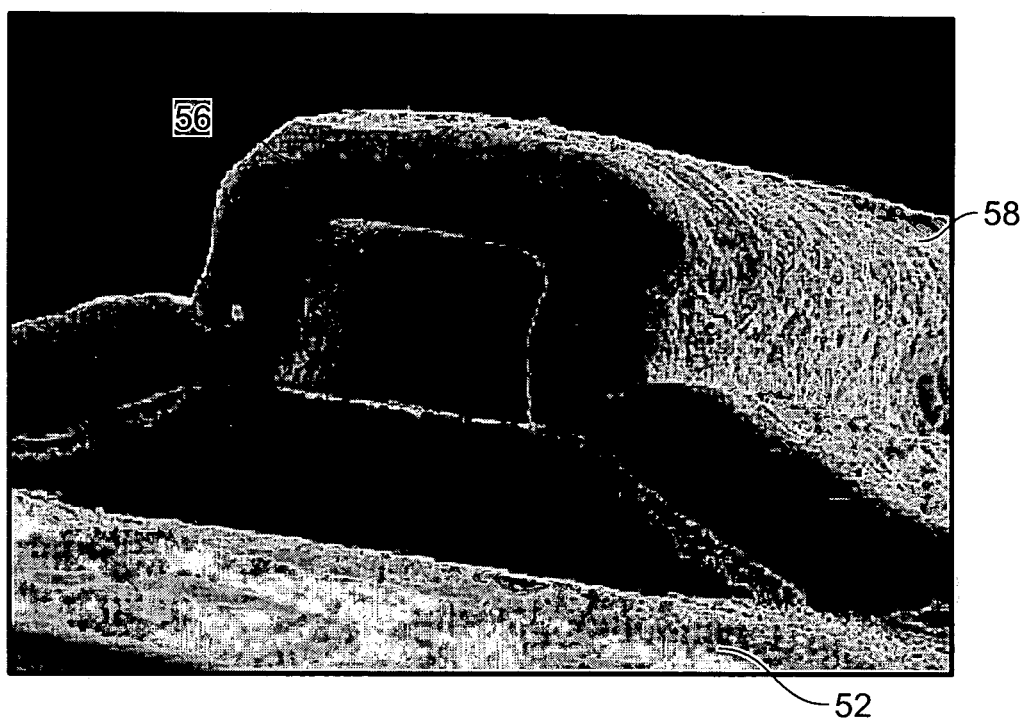
FIG. 8 is a photomicrograph of a transverse section of a drug-eluting stent in accordance with a preferred embodiment of the present invention.

FIGS. 7 and 8 illustrate an exemplary drug-delivery stent 50 in accordance with the present invention, which is depicted without the covering members 18 for purposes of clarity. Those of ordinary skill in the art will understand and recognize that alternative device designs and geometries are also contemplated by the present invention. Stent 50 is comprised generally of a plurality of structural elements 52 interconnected at a plurality of hinge regions 54 and defining a plurality of interstices 56 bounded by the plurality of structural elements and the plurality of hinge regions 54. As described above, the material used to fabricate the inventive device has a Z-axis wall thickness in the device material. The inventive device 50 incorporates at least one of a plurality of internal cavities 56 within the wall thickness of the material used to form the implantable device or endoluminal stent 50. The plurality of internal cavities 56 are preferably positioned in the plurality of structural elements 52 and are preferably not present in the hinge regions 54.

A plurality of micropores 58 are provided and communicate between a external surface of the device 50 and one of the plurality of internal cavities 56. As noted above, the plurality of micropores 58 are dimensioned to permit the bioactive agent to elute from the at least one of a plurality of internal cavities 56 and through the associated plurality of micropores 58 by diffusion, osmotic pressure or under the influence of a positive pressure applied by cellular in-growth into the plurality of internal cavities 56 or under positive pressure applied by stress and/or strain exerted on the plurality of internal cavities 56 due to deformation of the individual structural elements 52. The plurality of micropores 58 may furthermore be provided to communicate between an internal cavity 56 and either a luminal or abluminal surface of the inventive endoluminal stent, such as to expose the bioactive agent retained within the plurality of internal cavities 56 either to the blood stream, in the case of luminal micropores 58, and/or to adjacent tissue, in the case of abluminal micropores 58.

The at least one of a plurality of internal cavities 56 may be continuous or discontinuous throughout the inventive device 50. Specifically, in accordance with one preferred embodiment of the invention, the plurality of internal cavities 56 is discontinuous and each of the plurality of discontinuous internal cavities 56 reside within regions of the device 50 that are substantially non-load bearing regions of the device. In the particular embodiment illustrated in FIG. 7, the plurality of hinge regions 54 are devoid of internal cavities 56 because they are load bearing regions of the stent. It is contemplated, however, that regions of the inventive device 50 that are deformed or that are load bearing may include either continuous internal cavities 56 or discontinuous internal cavities within their wall thickness and provide for elution of a bioactive agent retained within the internal cavity positioned at the load bearing region under the influence of a positive motivating pressure exerted on the bioactive agent by deformation or load stress transferred by the device geometry to the internal cavity and to the bioactive agent. By providing regions of continuous and discontinuous internal cavities 56, a plurality of bioactive agents may be loaded into different internal cavities 56 for achieving different elution rates and pharmacological effects. FIG. 8 is a photomicrograph illustrating a transverse cross-sectional view through an individual structural element 52 illustrating the internal cavity 56 and the construction of the structural element 53 in which there is a base layer of material and a cap-layer of material overlaying and enclosing the base layer to form the internal cavity 56.

Each of the above-described preferred embodiments of the present invention may be fabricated by a number of methods. In accordance with present invention, it is contemplated that either forming wrought metal parts, such as capillary tubing, into the implantable device or forming the implantable devices by vacuum deposition techniques are the preferred method of making the implantable structural elements of the present invention. Where an implantable device is to be fabricated of a plurality of individual tubular elements, preexisting microtubular members having an outer diameter, for example, between 60 and 400 µm and a wall thickness of between 10 and 350 µm, may be employed to fabricate extremely small dimensioned devices suitable for intracranial or coronary artery applications. The microtubular members may be formed into a cylindrical endoluminal device, such as by braiding or bending and joining microtubular members together by spot welding. Where ends of the microtubular members are formed to be self-cannulating, the self-cannulating ends may be exposed on the abluminal surface of an endoluminal device at any point along the longitudinal axis thereof. The plurality of openings passing through the wall of each of the individual tubular elements may be formed by microdrilling the openings through the wall and into the internal cavity or lumen of the individual tubular members. The plurality of openings may be laser cut, etched or formed by EDM methods, and may be formed either pre- or post-formation of the tubular elements into the three-dimensional conformation of the implantable device.

Where an implantable device is to be formed from non-preexisting structural elements, vacuum deposition techniques may be employed to form the implantable structural body, such as sputtering, reactive ion etching, chemical vapor deposition, plasma vapor deposition, or the like, as are known in the microelectronics fabrication arts and are more fully described in commonly assigned U.S. Pat. No. 6,379,383, issued Apr. 30, 2002 and commonly assigned U.S. patent application Ser. No. 10/211,489, published as U.S. Published Patent Application No. 20030059640 published Mar. 27, 2003, both of which are hereby incorporated by reference as teaching methods of fabrication of implantable materials using physical vapor deposition processes.

The internal chambers, the plurality of openings and the cover members may each be formed during deposition. In order to form these elements by vacuum deposition, the vacuum deposition process may be modified requisite patterns of sacrificial material to form the regions of the internal chambers and openings, over a base layer of structural material, then depositing a second layer of structural material over the sacrificial material and the base layer. The sacrificial material may then be removed, such as by etching, to leave the internal cavities and plurality of openings formed within the deposited bulk material. The plurality of cover members may be formed by depositing a layer of cover material, then defining the cover members in the layer of cover material, such as by laser etching to define the cantilever-like cover members in the cover material.

Figure 9A:
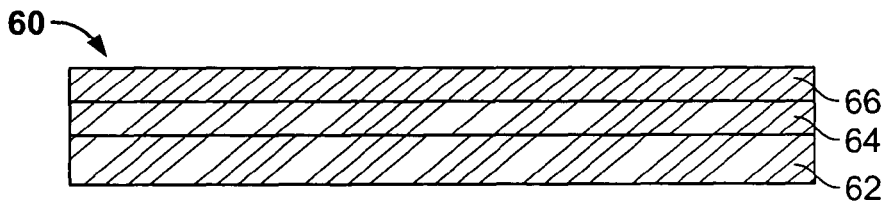
FIGS. 9A-9G are sequential cross-sectional views illustrating the method of fabricating the inventive drug eluting implantable medical device in accordance with the present invention.
Figure 9B:
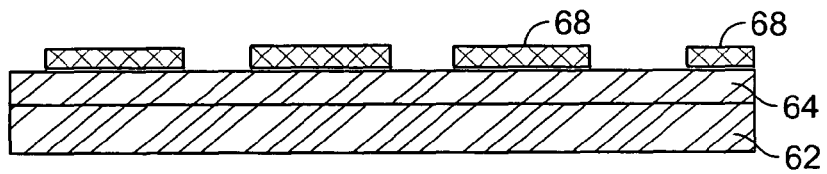
Figure 9C:
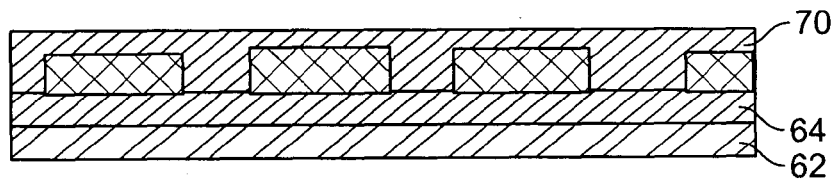
Figure 9D:
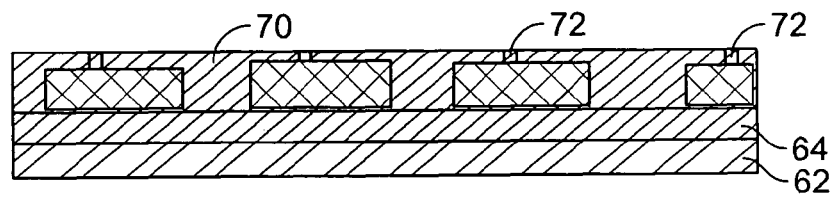
Figure 9E:
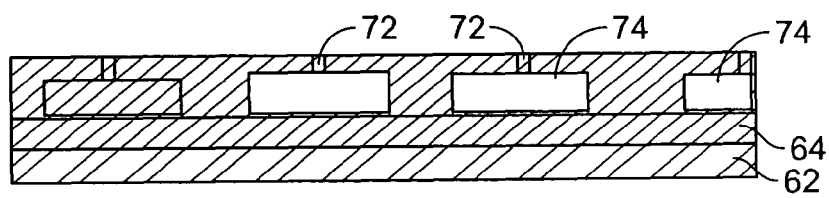
Figure 9F:
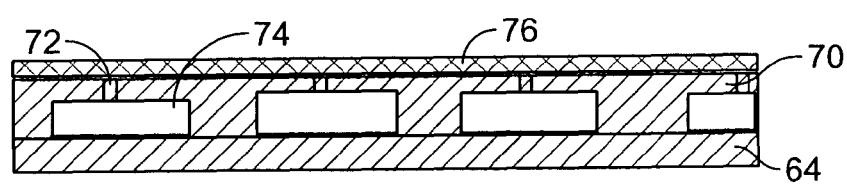
Figure 9G:
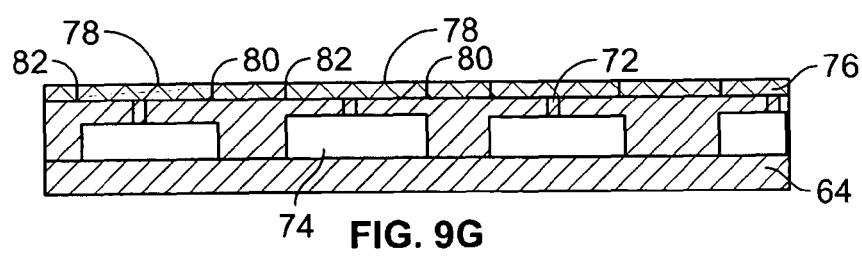

An exemplary method 60 for making the inventive drug-eluting medical device of the present invention is illustrated, sequentially, in FIGS. 9A through 9G. As depicted in FIG. 9A, a substrate 62 is provided; a first layer of biocompatible material 64 is deposited onto the substrate 62, followed by a sacrificial material layer 66. In FIG. 9B, the following step entails patterning the sacrificial material layer 66 to leave patterned sections 68 of the sacrificial layer 66. The pattern sections 68 will, as described hereinafter, form the internal chambers 21 of the inventive device. A second layer of biocompatible material 70 is then deposited onto the patterned sections 68 and the first layer of biocompatible material 64 as illustrated in FIG. 9C. As illustrated in FIG. 9D, a plurality of openings 72 are formed in the second layer of biocompatible material 70 and communicate with the patterned sections 68 of the sacrificial material layer 66. Then, as illustrated in FIG. 9E, the sacrificial material remaining in the patterned sections 68 is removed through the openings 72 to leave interior chambers 72 bounded entirely by the second layer of biocompatible material 70 and the first layer of biocompatible material 64. A third layer of biocompatible material 76 is then provided to cover the second layer of biocompatible material 70 and the plurality of openings 72 therein, as illustrated in FIG. 9F. This third layer of biocompatible material 76 may have been preformed with a plurality of cantilever members 78 having separation gaps 80 between adjacent cantilever members 78 and adhesion regions 82 formed between the gap 80 and the opening 72 which the cantilever member 78 covers, as illustrated in FIG. 9G. Those skilled in the art will appreciate that the third layer of biocompatible material may be provided as a discrete layer of material or may consist of a plurality of individual cantilever members 78 each coupled to the second layer of biocompatible material 70 at adhesion regions 82. The third biocompatible material 76 may be deposited directly onto the second layer of biocompatible material 70, then the plurality of individual cantilever members 78 formed, such as by laser cutting or selective etching. However, it will be important to interpose a sacrificial interlayer mask which covers the second biocompatible layer 70 and the plurality of openings 72, but exposes only the adhesion regions 82 so that, after removal of the sacrificial interlayer mask, the plurality of cantilever members 78 are free to deflect from and open the plurality of openings 72.

Regardless of which fabrication method is employed, the bioactive agent must be loaded into the internal cavities of the implantable device. Loading of the bioactive agent may be accomplished by flowing a liquid or semi-liquid state of the bioactive agent through the plurality of openings and into the internal cavities, either throughout the entire device or in regions of the implantable device. Flow loading may be facilitated by applying positive pressure, temperature change or both, such as is used in hot isostatic pressing (HIP). In HIP the pressurizing medium is typically a gas, and the process is carried out at elevated temperatures for specific time periods. While HIP is typically utilized to densify materials, to heal casting defects and voids, or to bond similar or dissimilar materials it may be used to drive a fluid or semi-fluid from external the implantable device into the internal cavities of the implantable device. Alternative, diffusion-mediated loading, osmotic loading or vacuum loading may be employed to load the bioactive agent into the internal cavities.

While the present invention has been described with reference to its preferred embodiments, those of ordinary skill in the art will understand and appreciate that variations in structural materials, bioactive agents, fabrication methods, device configuration or device indication and use may be made without departing from the invention, which is limited in scope only by the claims appended hereto.

What is claimed is:

1. An implantable drug-eluting medical device, comprising a first stent member having a plurality of wall surfaces defining a z-axis thickness of the first stent member to form the implantable drug-eluting medical device, at least a first internal chamber enclosed entirely within the z-axis thickness of the first stent member, at least a first of a plurality of openings communicating between the first internal chamber and at least a first of the plurality of wall surfaces and through a portion of the z-axis thickness of the first stent member, a first bioactive agent disposed within the first internal chamber, and a plurality of metal cover members disposed upon the first of the plurality of wall surfaces, at least a first of the plurality of metal cover members associated with the first opening, each of the plurality of metal cover members having a first position which covers and occludes an associated one of the plurality of openings and a second position which uncovers said associated opening, wherein one of shape memory properties or superelastic properties of the plurality of metal cover members actuate the plurality of metal cover members to pivot between the first position and the second position upon encountering a defined stimulus, and wherein in the second position each of the plurality of metal cover members projects outwardly from the first stent member.

2. The implantable drug-eluting medical device according to claim 1, wherein the stimulus is an exogenous stimulus applied transcutaneously to the medical device.

3. The implantable drug-eluting medical device according to claim 1, wherein the stimulus is selected from the group consisting of endogenous physical, electrical, thermal or chemical stimuli.

4. The implantable drug-eluting medical device according to claim 1, wherein the first stent member is selected from the group consisting of a stent, covered stent and vascular graft.

5. The implantable drug-eluting medical device according to claim 1, wherein the first stent member comprises a stent having a plurality of interconnected individual structural elements, at least some of the plurality of interconnected individual structural elements having the at least a first internal chamber, wherein each of the at least a first internal chamber has at least one of the plurality of openings communicating between the at least a first internal chamber and external the structural elements within which the at least a first chamber is disposed through a portion of the thickness of the structural elements, the at least one bioactive agent disposed within the at least a first internal chamber, and at least one of the plurality of metal cover members operably associated with the at least one of the plurality of openings.

6. The implantable drug-eluting medical device according to claim 1, wherein the first stent member and the plurality of metal cover members each comprise a material selected from the group consisting of nickel-titanium alloy, nickel-titanium-tantalum alloy, and chromium-cobalt alloy.

7. The implantable drug-eluting medical device according to claim 1, wherein the first bioactive agent comprises a pharmacologically active agent selected from the group consisting of antibiotic drugs, antiviral drugs, neoplastic agents, steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator, urokinase, hirudin, streptokinase, antiproliferative agents, antioxidants, antimetabolites, thromboxane inhibitors, non-steroidal and steroidal anti-inflammatory drugs, immunosuppresents, beta and calcium channel blockers, genetic materials including DNA and RNA fragments, complete expression genes, antibodies, lymphokines, growth factors, vascular endothelial growth factor, fibroblast growth factor, prostaglandins, leukotrienes, laminin, elastin, collagen, nitric oxide, integrins, paclitaxel, taxol, rapamycin, rapamycin derivatives and analogues, sirolimus, rapamune, tacrolimus, dexamethasone, everolimus, ABT-578 and growth factors.

8. An endoluminal stent, comprising a generally tubular member having a central lumen passing longitudinally through the tubular member and open at opposing ends of the tubular member, a luminal surface and an abluminal surface and a wall thickness defined therebetween, at least one internal chamber defined entirely within the wall thickness in at least some portions of the tubular member, a plurality of openings communicating between the at least one internal chamber and at least one of the luminal surface or abluminal surface through at least a portion of the wall thickness, at least one bioactive agent disposed in the at least one internal chamber and a plurality of metal cover members operably associated with the plurality of openings and each metal cover member having a closed position which occludes an associated one of the plurality of openings and an open position which permits the at least one bioactive agent to elute from the at least one internal chamber and through the associated one of the plurality of openings, wherein shape memory properties or superelastic properties of the plurality of metal cover members actuate the plurality of metal cover members to pivot between the closed position and the open position upon encountering a defined stimulus, and wherein in the open position each metal cover member projects outwardly from the luminal surface or the abluminal surface to a point outside the wall thickness.

9. The endoluminal stent according to claim 8, wherein the tubular member and the plurality of metal cover members comprise a material selected from the group consisting of nickel titanium alloy, and chromium-cobalt alloy.

10. The endoluminal stent according to claim 9, wherein at least one of the tubular member and the plurality of metal cover members are fabricated of at least one biocompatible thin metallic film.

11. The endoluminal stent according to claim 8, wherein the at least one bioactive agent comprises a pharmacologically active agent selected from the group consisting of antibiotic drugs, antiviral drugs, neoplastic agents, steroids, fibronectin, anti-clotting drugs, anti-platelet function drugs, drugs which prevent smooth muscle cell growth on inner surface wall of vessel, heparin, heparin fragments, aspirin, coumadin, tissue plasminogen activator, urokinase, hirudin, streptokinase, antiproliferative agents, antioxidants, antimetabolites, thromboxane inhibitors, non-steroidal and steroidal anti-inflammatory drugs, immunosuppresents, beta and calcium channel blockers, genetic materials including DNA and RNA fragments, complete expression genes, antibodies, lymphokines, growth factors, vascular endothelial growth factor, fibroblast growth factor, prostaglandins, leukotrienes, laminin, elastin, collagen, nitric oxide, integrins, paclitaxel, taxol, rapamycin, rapamycin derivatives and analogues, sirolimus, rapamune, tacrolimus, dexamethasone, everolimus, ABT-578 and growth factors.

12. The endoluminal stent according to claim 8, wherein the tubular member comprises a plurality of interconnected structural elements defining walls of the tubular member, a plurality of discontinuous interior chambers associated with at least some of the plurality of structural elements, the plurality of openings communicating between each of the plurality of discontinuous interior chambers and external the stent, the at least one bioactive agent disposed within the plurality of discontinuous interior chambers, and at least one of the plurality of metal cover members associated with the plurality of openings.

13. An implantable drug-eluting medical device, comprising:
   a first metal layer having a first wall surface and a second wall surface,
   a second metal layer disposed upon the second wall surface of the first metal layer, wherein the second metal layer defines at least a first internal chamber entirely enclosed by the second metal layer and the second wall surface of the first metal layer, and at least one of a plurality of openings communicating between the first internal chamber and external the second metal layer to form the implantable drug-eluting medical device;
   a bioactive agent disposed within the first internal chamber; and
   a third metal layer including a plurality of metal cover members disposed upon the second metal layer and associated with the plurality of openings, each of the plurality of metal cover members having a first position which covers and occludes an associated opening of the plurality of openings and a second position which uncovers the associated opening, wherein one of shape memory properties or superelastic properties of the plurality of metal cover members actuate the plurality of metal cover members to pivot between the first position and the second position upon encountering a defined stimulus, such that in the second position each metal cover member projects outwardly from the second metal layer.

14. The implantable drug-eluting medical device according to claim 13, wherein the stimulus is an exogenous stimulus applied transcutaneously to the medical device.

15. The implantable drug-eluting medical device according to claim 13, wherein the stimulus is selected from the group consisting of endogenous physical, electrical, thermal or chemical stimuli.

16. The implantable drug-eluting medical device according to claim 13, wherein the metal layers are selected from the group consisting of a stent, covered stent and vascular graft.

17. The implantable drug-eluting medical device according to claim 13, wherein each of the plurality of metal cover members is fabricated from a nickel titanium alloy or a chromium-cobalt alloy.

* * * * *